(12) United States Patent
Butters et al.

(10) Patent No.: US 10,085,807 B2
(45) Date of Patent: Oct. 2, 2018

(54) ROD CONTOURING ALIGNMENT LINKAGE

(71) Applicant: Stryker European Holdings I, LLC, Kalamazoo, MI (US)

(72) Inventors: Joshua A. Butters, Chandler, AZ (US); Jeffery Arnett, Gilbert, AZ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 69 days.

(21) Appl. No.: 14/662,988

(22) Filed: Aug. 3, 2015

(65) Prior Publication Data
US 2015/0327942 A1 Nov. 19, 2015

Related U.S. Application Data

(63) Continuation of application No. 11/904,029, filed on Sep. 25, 2007, now Pat. No. 9,011,447.
(Continued)

(51) Int. Cl.
*A61B 17/70* (2006.01)
*A61B 19/00* (2006.01)
(Continued)

(52) U.S. Cl.
CPC .......... *A61B 19/46* (2013.01); *A61B 17/7002* (2013.01); *A61B 17/7074* (2013.01);
(Continued)

(58) Field of Classification Search
CPC .................................. A61B 17/7074–17/7092
See application file for complete search history.

(56) References Cited

U.S. PATENT DOCUMENTS 5,531,751 A * 7/1996 Schultheiss ........ A61B 17/1615
606/104
RE36,221 E 6/1999 Breard et al.
(Continued)

FOREIGN PATENT DOCUMENTS

DE 29710979 U1 8/1997
DE 19726754 A1 2/1999
(Continued)

OTHER PUBLICATIONS

Charles Hartjen; The Atavi System, Surgical Technique Brochure. Endius, p. 1-17, undated.
(Continued)

*Primary Examiner* — Jan Christopher Merene
*Assistant Examiner* — Steven Cotroneo
(74) *Attorney, Agent, or Firm* — Lerner, David, Littenberg, Krumholz & Mentlik, LLP

(57) ABSTRACT

Pedicle screws are designed to provide polyaxial coupling to pedicles of a vertebra. Intermediate pieces are attached to the pedicles screws and receive extender shafts. Extenders are inserted in the intermediate piece. The extenders project the anatomic points located in the cage outside the patient's body to facilitate proper contouring of a rod. An alignment linkage is used to ensure that the extenders are parallel to each other. The alignment linkage includes a linkage frame, an articulating linkage and a locking member. The articulating linkage has all rotational degrees of freedom and thereby adapts to any varying trajectories of the extenders and distance between the extenders. The alignment linkage includes a locking member with a pop-up indicator. The pop-up indicator notifies the users when the locking member is tightened with two of the extenders in non-parallel configuration.

21 Claims, 16 Drawing Sheets

Related U.S. Application Data

(60) Provisional application No. 60/847,157, filed on Sep. 25, 2006.

(51) Int. Cl.
*A61B 17/86* (2006.01)
*A61B 17/88* (2006.01)
*A61B 90/00* (2016.01)

(52) U.S. Cl.
CPC .......... *A61B 17/86* (2013.01); *A61B 17/8863* (2013.01); *A61B 90/06* (2016.02); *A61B 17/708* (2013.01); *A61B 17/7037* (2013.01); *A61B 2090/061* (2016.02)

(56) References Cited

U.S. PATENT DOCUMENTS

| | | | |
|---|---|---|---|
| 6,090,113 A | 7/2000 | Le Couedic et al. | |
| 6,123,707 A | 9/2000 | Wagner | |
| 6,235,028 B1 * | 5/2001 | Brumfield | A61B 17/7083 606/53 |
| 6,332,780 B1 | 12/2001 | Traxel et al. | |
| 6,485,518 B1 | 11/2002 | Cornwall et al. | |
| 6,530,929 B1 | 3/2003 | Justis et al. | |
| 7,008,422 B2 | 3/2006 | Foley et al. | |
| 7,011,660 B2 | 3/2006 | Sherman et al. | |
| 7,083,621 B2 | 8/2006 | Shaolian et al. | |
| 7,188,626 B2 | 3/2007 | Foley et al. | |
| 7,666,189 B2 * | 2/2010 | Gerber | A61B 17/7074 606/104 |
| 7,811,288 B2 * | 10/2010 | Jones | A61B 17/7091 606/279 |
| 8,157,809 B2 | 4/2012 | Butters et al. | |
| 8,177,817 B2 | 5/2012 | Fallin | |
| 8,506,574 B2 | 8/2013 | Butters et al. | |
| 8,894,655 B2 | 11/2014 | Fallin et al. | |
| 8,915,925 B2 | 12/2014 | Butters et al. | |
| 8,979,851 B2 | 3/2015 | Fallin et al. | |
| 2002/0072752 A1 * | 6/2002 | Zucherman | A61B 17/7074 606/99 |
| 2004/0034351 A1 | 2/2004 | Sherman et al. | |
| 2004/0138662 A1 * | 7/2004 | Landry | A61B 17/1604 606/86 A |
| 2004/0143265 A1 | 7/2004 | Landry et al. | |
| 2004/0147928 A1 | 7/2004 | Landry et al. | |
| 2004/0172022 A1 | 9/2004 | Landry et al. | |
| 2004/0215190 A1 | 10/2004 | Nguyen et al. | |
| 2004/0267279 A1 * | 12/2004 | Casutt | A61B 90/06 606/104 |
| 2005/0021031 A1 | 1/2005 | Foley et al. | |
| 2005/0038432 A1 | 2/2005 | Shaolian et al. | |
| 2005/0070917 A1 * | 3/2005 | Justis | A61B 17/1757 606/104 |
| 2005/0171540 A1 | 8/2005 | Lim et al. | |
| 2005/0234449 A1 * | 10/2005 | Aferzon | A61B 17/7089 606/86 A |
| 2005/0245928 A1 * | 11/2005 | Colleran | A61B 17/708 606/90 |
| 2006/0030839 A1 | 2/2006 | Park et al. | |
| 2006/0111714 A1 | 5/2006 | Foley | |
| 2006/0200135 A1 | 9/2006 | Sherman et al. | |
| 2006/0264934 A1 * | 11/2006 | Fallin | A61B 17/8863 606/86 A |
| 2007/0093824 A1 * | 4/2007 | Hestad | A61B 17/7032 606/261 |
| 2009/0099605 A1 | 4/2009 | Fallin et al. | |
| 2012/0197302 A1 | 8/2012 | Fallin | |
| 2014/0031871 A1 | 1/2014 | Fallin et al. | |
| 2015/0073428 A1 | 3/2015 | Butters et al. | |

FOREIGN PATENT DOCUMENTS

| | | |
|---|---|---|
| DE | 10027988 | 1/2002 |
| EP | 0528177 | 2/1993 |
| EP | 1767161 A1 | 3/2007 |
| SU | 839513 | 6/1981 |
| WO | 9514437 | 6/1995 |
| WO | 0141681 A1 | 6/2001 |
| WO | 04041100 | 5/2004 |
| WO | 2006091863 | 8/2006 |
| WO | 06/125029 | 11/2006 |

OTHER PUBLICATIONS

Diapason, Surgical Texchnique Catalog, Diapasan Spinal System, Jan. 2002.
Sofamor Danek; Sextant CD Horizon Sextant Rod Insertion System, Surgical Technique, Techniques, p. 1-29, 2003.
European Search Report, EP 10160769, dated May 26, 2010.

* cited by examiner

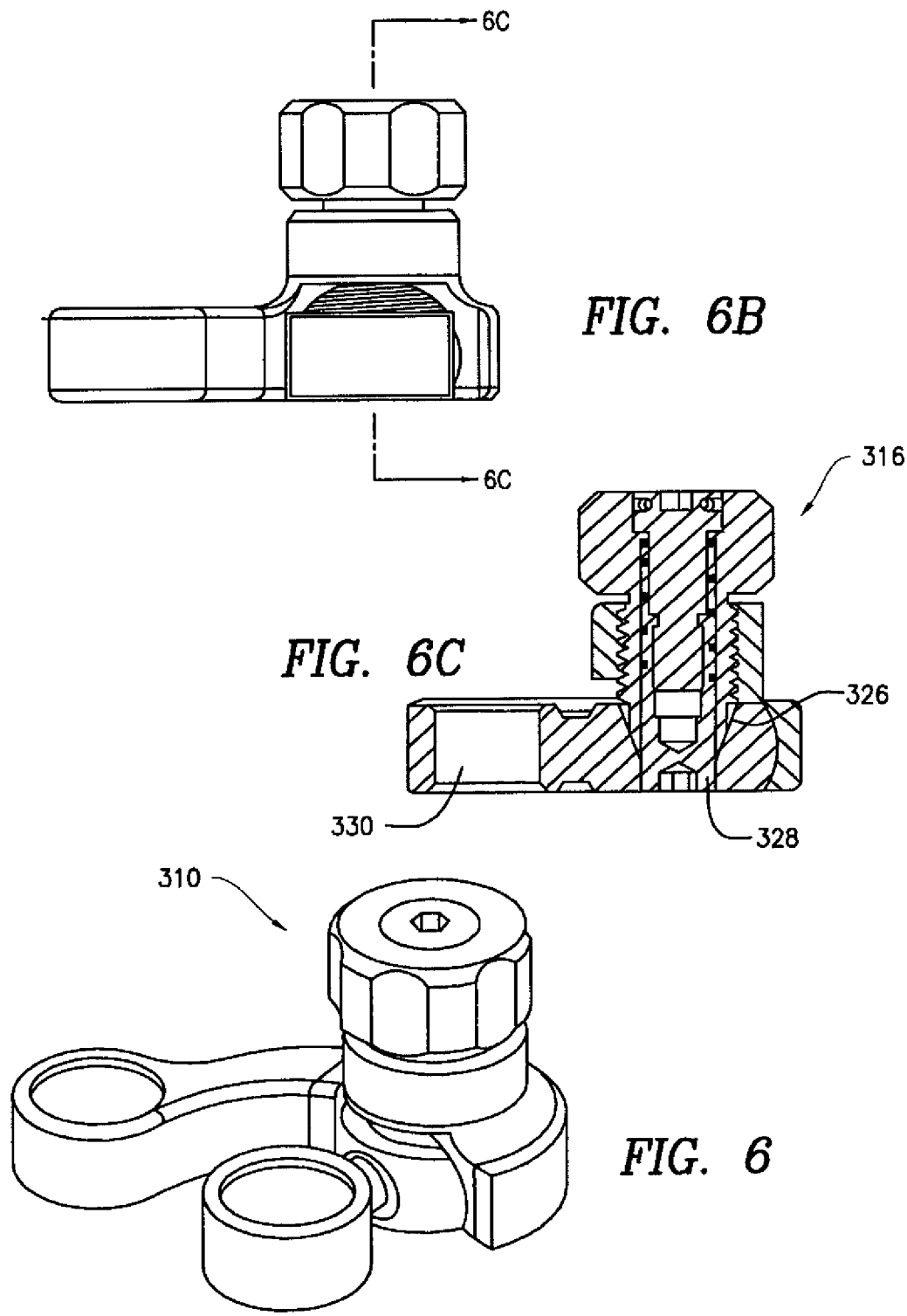

ROD CONTOURING ALIGNMENT LINKAGE

CROSS-REFERENCE TO RELATED APPLICATIONS

This application is a continuation of U.S. application Ser. No. 11/904,029, filed Sep. 25, 2007, which claims priority from Provisional Application No. 60/847,157, filed Sep. 25, 2006, the disclosures of which are hereby incorporated herein by reference.

BACKGROUND OF THE INVENTION

Field of the Invention

The present invention relates generally to the selection and configuration of implantable devices, and more particularly to alignment linkage for orthopedic implant configuration for posterior spinal fusion systems.

Brief Description of the Prior Art

A wide variety of orthopedic implants exist. Such implants are typically anchored to bones within the body. Every person has different bone structure; accordingly, implants must vary considerably in geometry to meet the needs of a broad range of patients. Sophisticated surgical navigation equipment may be used to properly locate these implants on the bone. However, such equipment is expensive and constitutes an added layer of complexity in the operating room. Visualization methods such as x-rays and fluoroscopy can also be utilized to help determine bone geometry. However, contact with the bones must often be made in order to provide a sufficiently accurate measurement of bony landmarks. Current procedures often involve the exposure of a relatively large area to permit such measurement.

According to new minimally invasive surgical (MIS) procedures, many orthopedic implants can be secured to bone through relatively small incisions. Unfortunately, if a larger incision must be made to permit bone measurement and implant selection or configuration, most of the beneficial effects of the MIS implantation procedure will be lost. Accordingly, there is a need in the art for bony landmark measurement and implant selection or configuration methods that can be carried out through small incisions. Such methods should be relatively simple and quick to perform, with comparatively simple instrumentation.

SUMMARY OF THE INVENTION

The present invention fills the need described above by providing a systems and methods for configuring and/or selecting implantable devices for posterior spinal fusion. The system includes pedicle screws designed to provide polyaxial coupling to pedicles of a vertebra. Pedicle screws have a cage shaped to receive a rod, and a screw that is able to extend from the cage along a plurality of relative orientations. Each cage has two arms that extend generally away from the screw and define a first slot and a second slot through which a rod can pass. Tightening of a nut in the arms of the cage presses the rod against the head of the screw to keep the rod in place within the slots and to lock the orientation of the screw with respect to the cage.

Intermediate pieces are attached to the pedicles screws to form passages for receiving projection shafts. Alternately, cannulas may be attached to pedicle to form the passages for receiving projection shafts. The connection between the intermediate pieces and the pedicle screws are snug, thereby making the intermediate pieces coaxial with the respective cages of the pedicle screws. Similarly, the cannulas are coaxial with respective cages of the pedicle.

Extenders are inserted in the intermediate piece. The extenders are in engagement with the pedicle screw. The extenders project the anatomic points located in the cage outside the patient's body to facilitate proper contouring of the rod. Thus, the space between the intermediate pieces need not be accessed to obtain the proper rod configuration. The extenders are coaxial with respective cages. However, if the extenders are not parallel to each other, projected anatomic points will not have the same spatial relationship (i.e., relative positioning) as the anatomic points in the cage. The proximal ends of the extenders have a geometry that mimics the geometry of the cages.

An alignment linkage is used to ensure that the extenders are parallel to each other. The alignment linkage includes a linkage frame, an articulating linkage and a locking member. The articulating linkage has all rotational degrees of freedom and thereby adapts to any varying trajectories of the extenders and distance between the extenders. The alignment linkage includes a locking member with a pop-up indicator. The pop-up indicator notifies the users when the locking member is tightened with two of the extenders in non-parallel configuration. Once the first and second extenders are locked in parallel position, the process is repeated using a second alignment linkage to lock the second and the third extender in mutually parallel position. Once the alignment linkages have been applied, the extenders are locked parallel and the projected anatomic points mimic the relative positioning of the anatomic points within the body.

A rod is seated in rod interfaces on the proximal end of the extenders for contouring. The first end of the rod is positioned in the rod interface of the first extender, the central portion is positioned in the rod interface of the second extender, and the second end is positioned in the rod interface of the third extender. Due to natural variations in spinal morphology, the rod interfaces may not be arranged in a straight line. Thus, the rod may need to be bent into the proper shape, for example, through the use of tooling such as pliers, a vice, or the like, so that it will lie properly within the rod interfaces. In the alternative the rod may simply be selected from a kit. After the rod has been configured or selected, the rod and the extenders may be removed from the operating site, leaving the pedicle screws in place. The cannulas or intermediate pieces, if used, may also be removed at this stage. The rod may be inserted subcutaneously and placed on the cages.

An object of the invention is to provide a system for projecting anatomic points located within a patient's body outside the patient's body. The system includes a first pedicle screws and a second pedicle screw, the first and the second pedicle screws are adapted to attach in a patient's body and have a first anatomic point and a second anatomic point located therein, respectively. A first extender and a second extender are connected to the first pedicle screw and the second pedicle screw, respectively. An alignment linkage having a first arm and a second arm is attached to the first extender and the second extender. The first arm and the second arm of the alignment linkage are rotatable with respect to each other. A locking screw is attached to the alignment linkage to lock the first and the second extenders in parallel orientation. When the extenders are parallel to each other, the first anatomic point and the second anatomic point are projected outside the patient's body to corresponding points on proximal ends of the first extenders and the second extender and the projected anatomic points mimic the relative position of the first and the second anatomic points within the body.

Another object of the invention is to provide a system for projecting anatomic points located within a patient's body outside the patient's body wherein the system has a first pedicle screws and a second pedicle screw. The first and the second pedicle screws attach in a patient's body and have a first anatomic point and a second anatomic point located within the body of the screws. A first extender and a second extender are connected to the first pedicle screws and the second pedicle screws respectively. A first alignment linkage having a first arm and a second arm is attached to the first extender and the second extender. The first arm and the second arm are rotatable with respect to each other. A pop-up pin is included in the first alignment linkage. The pop-up pin pops when one attempts to lock with each other the first and the second arm while the first extender and the second extender are not parallel to each other. The popping of the pin indicates that the anatomic points corresponding to the first anatomic point and the second anatomic point that are projected outside the patient's body to a corresponding points on the proximal end of the first extenders and the second extender do not accurately mimic the relative position of the first and the second anatomic points within the body.

Another object of the invention is to provide a method of projecting anatomic points located within a patient's body outside the patient's body. The projected anatomic points may be used to select or shape an implant to connect the anatomic points in the patient's body. The method includes implanting a first pedicle screw and a second pedicle screw in the patient's body and attaching a first extender and a second extender to the first pedicle screw and the second pedicle screw respectively. Next, the first extender and the second extender are locked in a mutually parallel position using an alignment linkage that has two limbs that are rotatably connected to each other. A first proximal end of the first extender and a second proximal end of the second extender may now be used as a proxy for a first anatomic point and a second anatomic point located in the patient's body.

BRIEF DESCRIPTION OF THE DRAWINGS

FIG. 6 is an isometric view of a rod contouring alignment linkage.

FIG. 6B is a side view of the rod contouring alignment linkage of FIG. 6.

FIG. 6C is a cross-sectional view of the rod contouring alignment linkage of FIG. 6 with the section taken along line A-A shown in FIG. 6B.

DETAILED DESCRIPTION OF THE PREFERRED EMBODIMENTS

The present invention relates to systems and methods for configuring and/or selecting devices to be implanted in the body. More particularly, the present invention relates to projecting anatomic points located within a patient's body outside the patient's body to facilitate selection or configuration of an implant that is to be implanted in the body between the anatomic points. Although the examples provided herein generally relate to contouring a rod for a posterior spinal fusion system, the present invention may be applied to any procedure in which the relative position and/or orientations of internal anatomic locations are to be measured or used to configure or select an implant.

Figure 1:
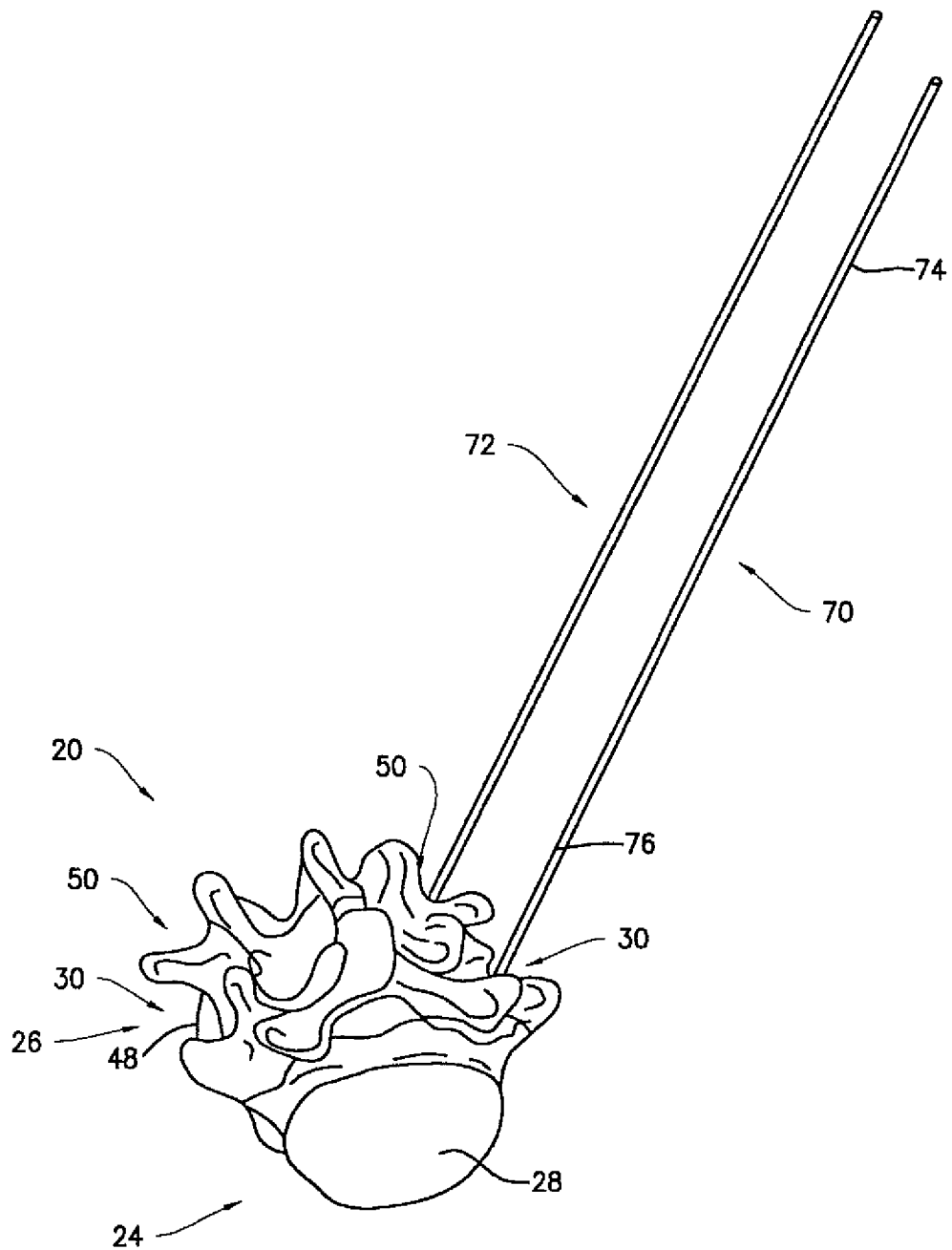
FIG. 1 is a perspective view of two adjacent vertebrae of a spine, with guide wire implanted in the pedicles of the right side.

Referring to FIG. 1, a perspective view illustrates a portion of a spine 20. As shown, the portion of the spine 20 illustrated in FIG. 1 includes a first vertebra 24, which may be the L5 (Fifth Lumbar) vertebra of a patient, and a second vertebra 26, which may be the L4 (Fourth Lumbar) vertebra of the patient. The systems and methods described hereafter may be applicable to any vertebra or vertebrae of the spine 20 and/or the sacrum (not shown). In this application, the term "vertebra" may be broadly interpreted to include the sacrum.

As shown, the first vertebra 24 has a body 28 with a generally disc-like shape and two pedicles 30 that extend posteriorly from the body 28. Similarly, the second vertebra 26 has a body 48 from which two pedicles 50 extend posteriorly. The vertebrae 24, 26 and/or the intervertebral disc (not shown) between them, may be damaged or diseased in some manner that makes it desirable to secure the vertebrae 24, 26 together in a manner that prevents relative motion between them. Accordingly, posterior spinal fusion may be employed to secure the pedicles 30, 50 together.

As further illustrated in FIG. 1, a first guide wire 70 may be inserted into the right side pedicle 30 of the first vertebra 24, and a second guide wire 72 may be inserted into the right-side pedicle 50 of the second vertebra 26. The distal ends 76 of the guide wires 70, 72 may be implanted by methods known in the surgical arts. A third guide wire 78 (see FIG. 2) may be positioned adjacent to the first and second guide wires 70, 72 as though the third guide wire 78 were implanted in the right-hand pedicle of a vertebra (not shown in FIG. 1 or 2) directly superior to the second vertebra 26. Accordingly, the method described herein may be used to secure together vertebrae on multiple levels, not just two adjacent vertebrae.

Dilators and cannula, and a variety of other guiding devices and dilation devices used in the surgical art may be used with the method described herein. A detailed description of such use is provided in commonly assigned patent application entitled "SYSTEM AND METHOD FOR ORTHOPEDIC IMPLANT CONFIGURATION" filed Jul. 8, 2005, Ser. No. 11/178,035, which is hereby incorporated by reference in its entirety.

Guide wires 70, 72, and 78 may be used to guide pedicle screws 140, 142 and 148 (see FIG. 2) to their implantation position on vertebrae 24, 26 and 28 respectively. The pedicle screws 140, 142 and 148 may be designed to provide polyaxial coupling to the associated pedicles. Pedicle screws 140, 142 and 148 each have a cage 152 (see FIGS. 2 and 3) shaped to receive a rod, and a screw 154 that passes through an aperture (not visible) of the cage 152 in such a manner that the screw 154 is able to extend from the cage 152 along a plurality of relative orientations. Thus, after the screw 154 has been implanted in a pedicle, the orientation of the cage 152 with respect to the screw 154 can still be altered. Each of the screws 154 has a lumen passing along the axis of the screw 154 so that the screws 154 can slide along the guide wires 70, 72, and 78 for accurate implantation in the pedicles.

Each cage 152 has two arms 156 that extend generally away from the screw 154 and define a first slot 158 and a second slot 160 through which a rod (not shown in FIG. 2 or 3) can pass. The closed ends of the slots 158, 160 are rounded in a manner that corresponds to the radius of the rod to be retained within the cage 152 to facilitate secure retention of the rod. The inward-facing surfaces of the arms 156 may be threaded to enable the arms 156 to receive a nut (not shown in FIG. 2 or 3). Tightening of the nut then presses the rod against the head (not shown) of the screw 154 to keep the rod in place within the slots 158, 160, and to lock the orientation of the screw 154 respect to the cage 152.

The pedicle screws 140, 142 and 148 represent only one of many types of connection elements that may be used in connection with the present invention. A variety of known devices may be used to secure a rod to a plurality of vertebra to provide posterior fusion.

Upon implantation in the pedicles, pedicle screws 140, 142 and 148 are positioned such that a first anatomic point 164, a second anatomic point 166, and a third anatomic point 168 are within the cages 152 of the first pedicle screw 140, the second pedicle screw 142, and the third pedicle screw 148, respectively. Upon installation of the rod, the axis of the rod is to pass through the anatomic points 164, 166 and 168.

Figure 2:
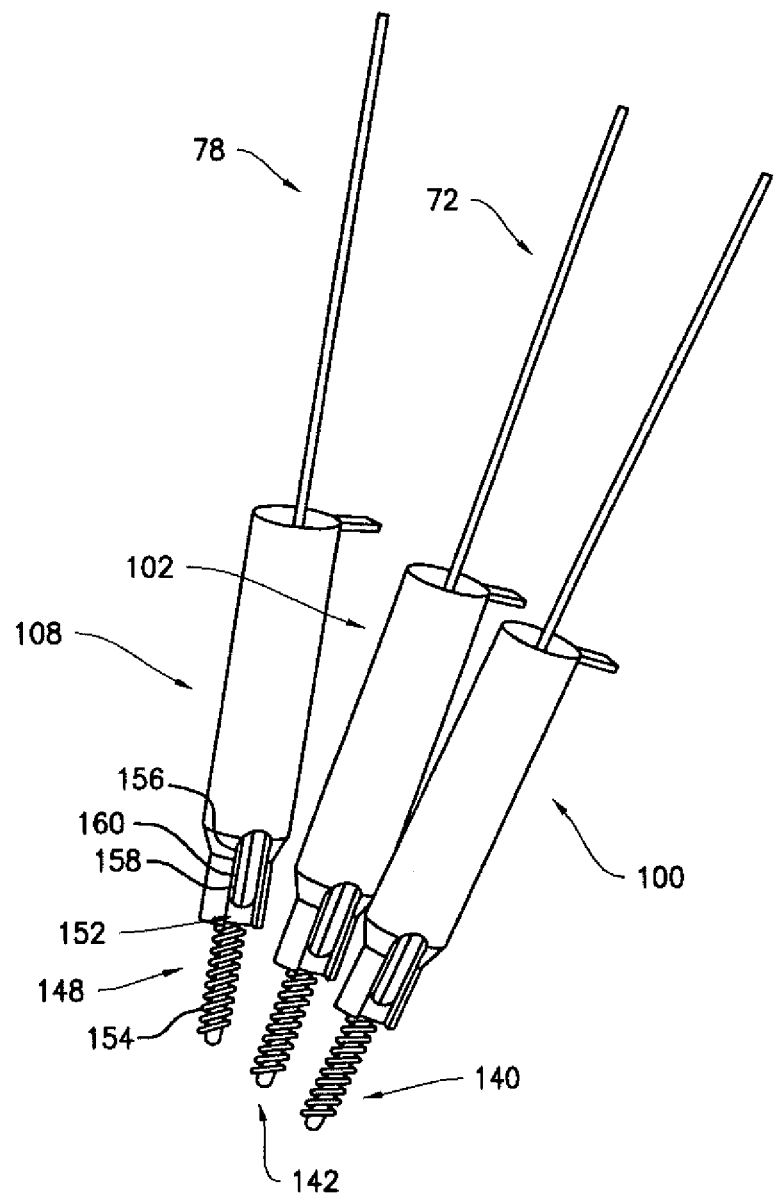
FIG. 2 is a perspective view showing guide wires, cannulas and pedicle screws implanted in three adjacent vertebrae (not shown).
Figure 3:
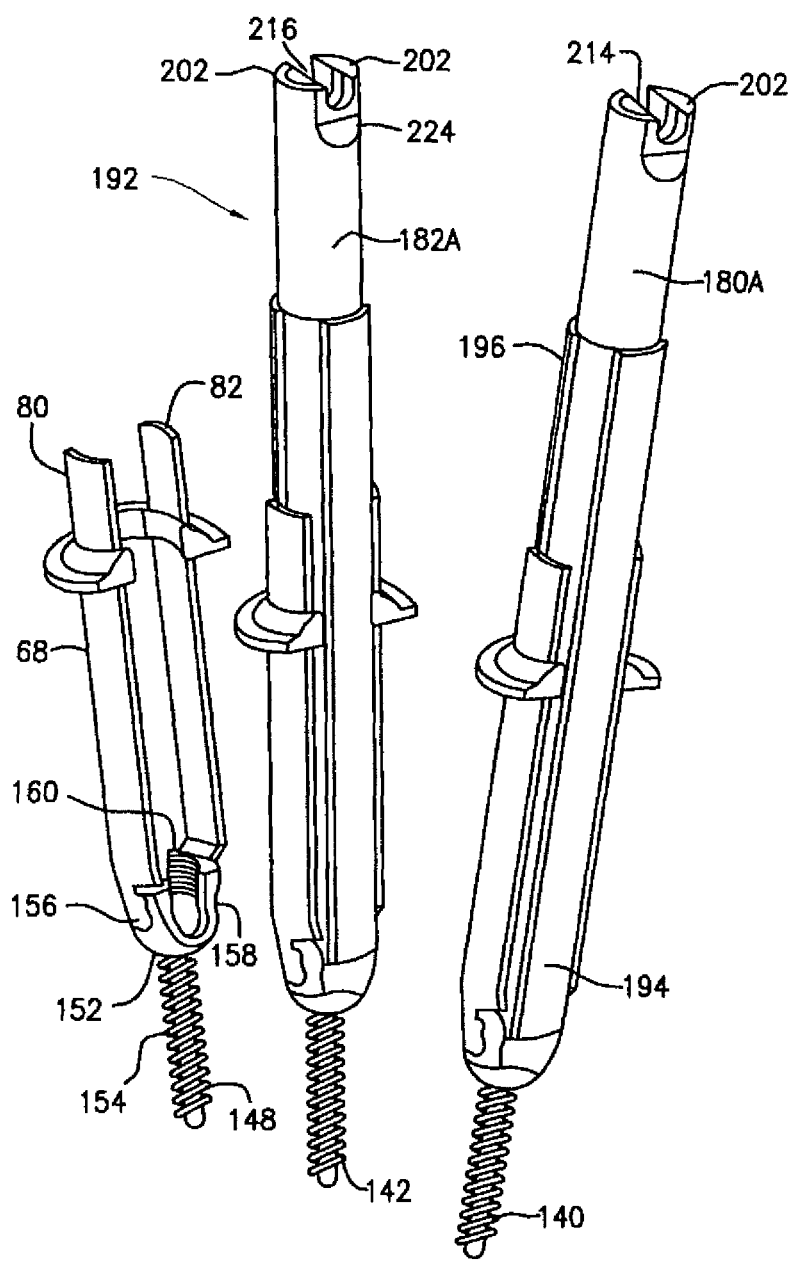
FIG. 3 is a perspective view showing pedicle screws implanted in three adjacent vertebrae (not shown), intermediate pieces and extenders.

FIG. 3 also shows intermediate pieces 80. Each intermediate piece 80 includes intermediate piece arms 82 and 88 forming a passage of fixed dimension. Ends of the intermediate piece arms 82 and 88 are connected to the arms 156 of the cage 152. The connection between the arms 156 and the intermediate piece arms 82 and 88 may be made in any suitable manner, for example, via a latch or a threaded joint. The intermediate pieces 80, when attached to the pedicles screws 140, 142 and 148, form a passage for receiving projection shafts 180A, 182A and 188A respectively. Alternately, cannulas 100, 102 and 108 (see FIG. 2) may be attached to pedicle screws 140, 142 and 148 to form a passage for receiving projection shafts 180, 182 and 188 respectively. The connection between the intermediate pieces 80 and the pedicle screws 140, 142 and 148 are snug, thereby making the intermediate pieces 80 coaxial with the respective cages 152 of the pedicle screws 140, 142 and 148. Similarly, the cannulas 100, 102 and 108 are coaxial with respective cages 152 of the pedicle screws 140, 142 and 148. Intermediate pieces 80 may be used in place of cannulas 100, 102 and 108 or vice versa.

Figure 4:
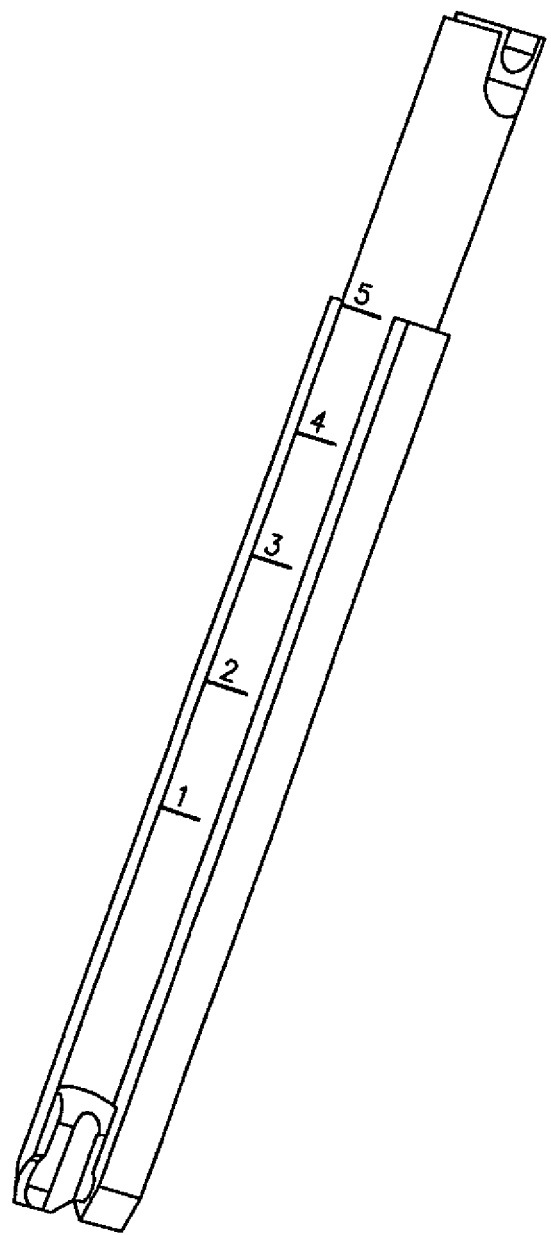
FIG. 4 is a perspective view showing an extender.
Figure 4D:
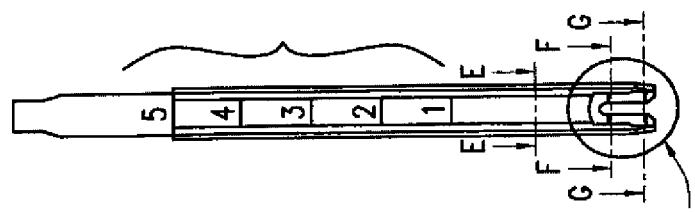
FIG. 4D is an enlarged view showings detail of construction of the distal end of the extender of FIG. 4.
Figure 4C:
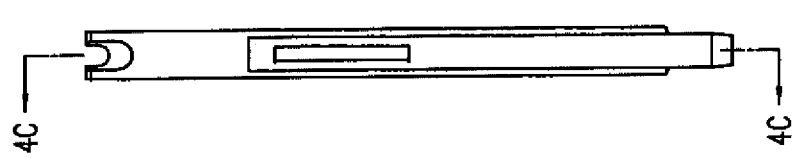
FIG. 4C is a cross sectional view of the extender of FIG. 4.
Figure 4B:
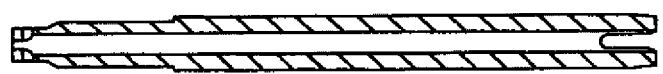
FIG. 4B is a side view of the extender of FIG. 4.
Figure 4A:
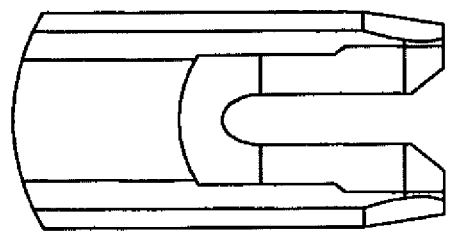
FIG. 4A is a front view of the extender of FIG. 4.

FIG. 3 illustrates intermediate pieces 80 with first extender 180A and a second extender 182A. Each intermediate piece includes two arms. A third extender 188A (not shown in FIG. 3) may also be inserted in the third intermediate piece shown in FIG. 3. First second and third extenders 180A, 182A and 188A are in engagement with the pedicle screw 140, 142 and 148 respectively. FIG. 4 illustrates the first, second or third extender; FIGS. 4A, 4B, 4C and 4D illustrate various details of construction of the extender of FIG. 4. The engagement between the extenders 180A, 182A, and 188A (or 180, 182 and 188) and pedicle screws 140, 142 and 148 respectively may be a threaded connection or a snap fit or a latch or any other suitable means for engagement. The extenders 180A, 1802A and 188A (or 180, 182 and 188 seen in FIG. 5) are used to respectively project the anatomic points 164, 166 and 168 outside the patient's body to facilitate proper contouring of the rod (not shown in FIG. 2 or 3). Thus, the space between the intermediate pieces 80 need not be accessed to obtain the proper rod configuration. The extenders 180A, 1802A, 188A, (or 180, 182 and 188) are coaxial with respective cages 152. The coaxiality of the extenders 180, 182, 188 (or 180A, 182A, 188A) with the cages 152 enables rod interfaces 200 (see FIG. 5) to provide a linear transformation of each of the first, second, and third anatomic points 164, 166 and 168 to points outside the body. More precisely, the first extender 180A (or 180) projects the first anatomic point 164 along the length of the first extender 180A (or 180) to a first projected point 214 within the rod interfaces 200 of the first extender. The second and third anatomic points 166, 168 are similarly projected to second and third projected points 216, 218. However, if the extenders 180A, 182A and 188A (or 180, 182 or 188) are not parallel to each other, projected points 214, 216, 218 will not have the same spatial relationship (i.e., relative positioning) as the anatomic points 164, 166, 168.

Figure 5:
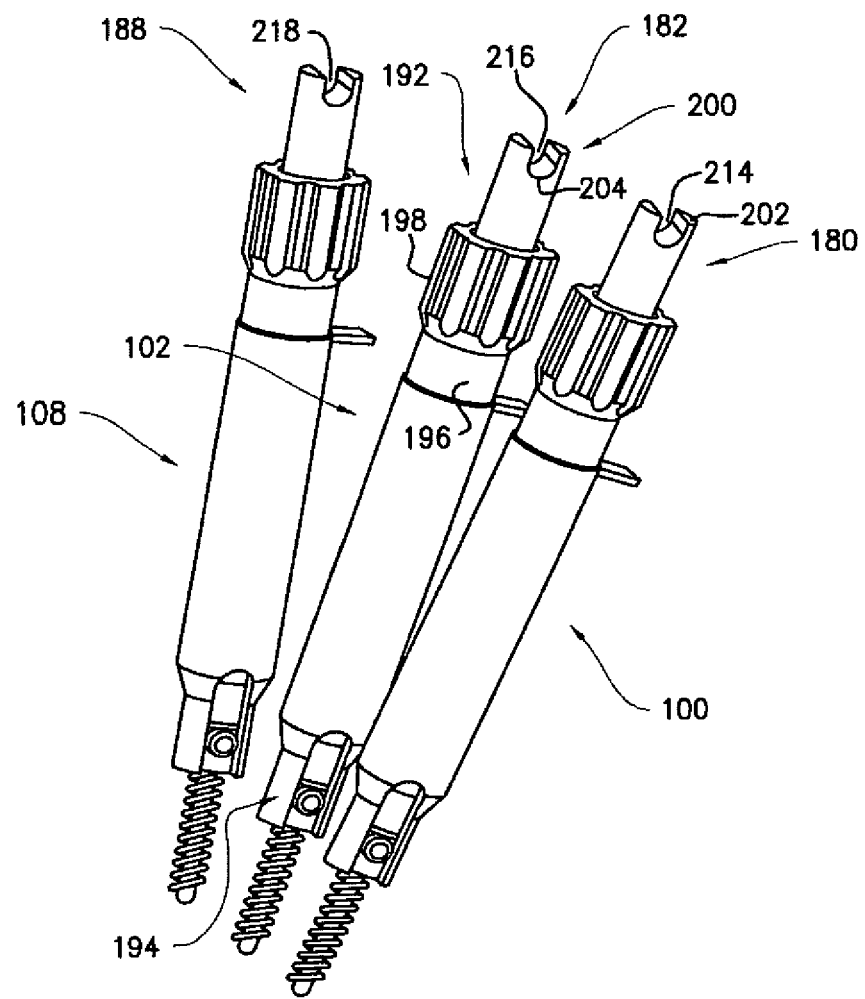
FIG. 5 is a perspective view of the cannulas and pedicle screws of FIG. 2 with extenders connected to the pedicle screws.
Figure 6A:
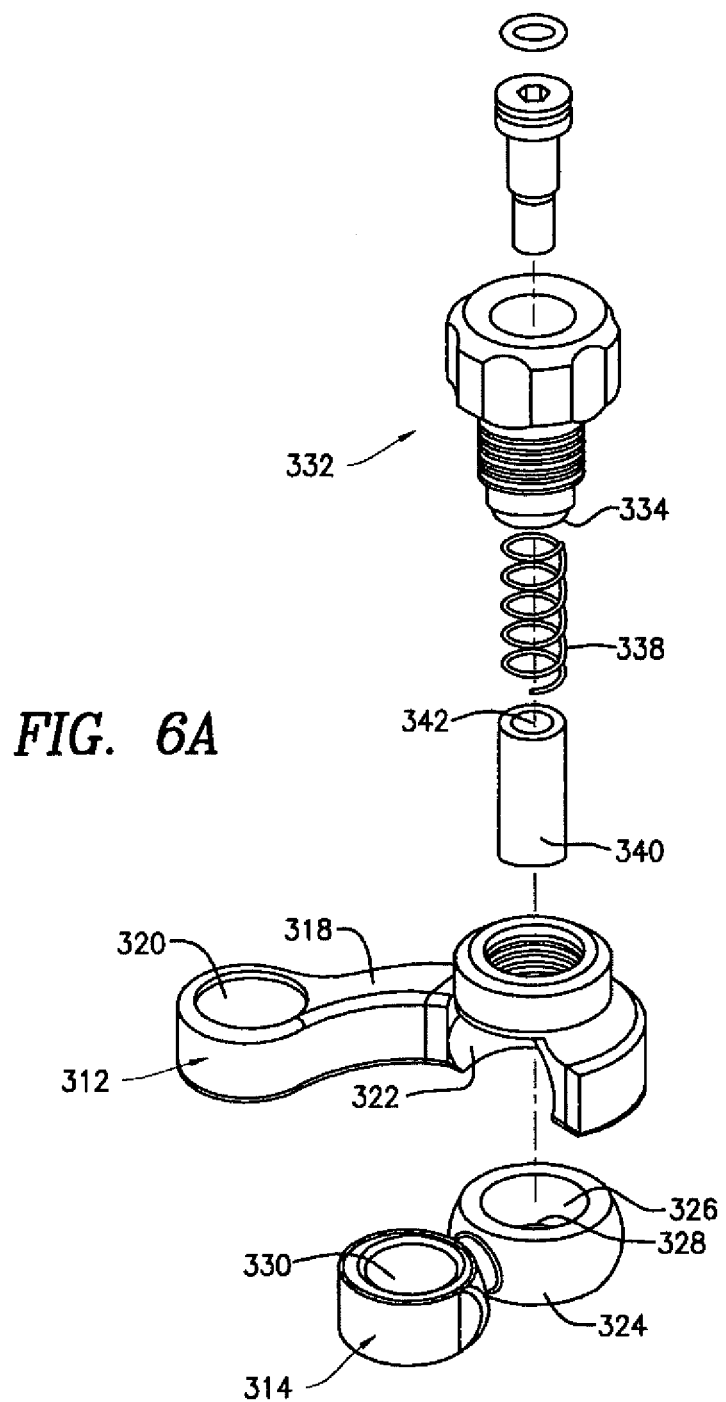
FIG. 6A shows various parts of the rod contouring alignment linkage in a disassembled state.

Referring to FIG. 5, a perspective illustrates the cannulas 100, 102 and 108 and the pedicle screws 140, 142 and 148 of FIG. 2, with a first extender 180, a second extender 182, and a third extender 188 inserted into engagement with the cannulas 100, 102, 108 and pedicle screws 140, 142, 148. In the embodiment of FIGS. 2 and 5, each of the extenders 180, 182, 188, 180A, 182A and 188A (not shown) has a proximal portion 192, a distal portion 194, and a stem 196 extending between the proximal portion 192 and distal portion 194. The proximal portion 192 of each of the extenders 180, 182, 188 has a handle 198 that may be grasped by hand or by tool. Each proximal portion 192 of the extenders 180, 182, 188, 180A, 182A and 188A also has an implant interface, which may take the form of a rod interface 200. Each rod interface 200 is shaped to receive a portion of a rod to facilitate contouring of the rod so that the contoured rod will pass through the anatomic points 164, 166, 168 within the cages 152 of the implanted pedicle screws 140, 142, 148.

Each of the rod interfaces 200 has two arms 202 that extend generally away from the remainder of the corresponding extender 180, 182, 188, 180A, 182A or 188A. The arms 202 of each rod interface 200 define a trough 204 through which a rod (not shown) can pass. The base of the trough 204 is rounded in a manner that corresponds to the radius of the rod to be retained within the cage 152 to facilitate secure retention of the rod. The arms 202 are similar in configuration to the arms 156 of the cage 152 of the corresponding pedicle screw 140, 142 and 148, and the trough 204 is similar to a trough defined by the first and second slots 158, 160 of the cage 152. Accordingly, the rod interfaces 200 mimic the geometry of the cages 152 of the pedicle screws 140, 142 and 148.

The extenders 180, 182 and 188, shown in FIG. 5 and extenders 180A, 182A and 188A shown in FIG. 3 represent only two of many potential extender configurations that may be used in connection with the present invention. Other extender configurations may be advantageous, particularly if the cannulas, dilators, connection elements, intermediate pieces or guidance members employed are different from those of FIGS. 3 and 5. However, the extenders 180A, 182A and 188A (or 180, 182 and 188) must be parallel to each other for the projected points 214, 216 and 218 to have the same spatial relationship (i.e., relative positioning) as anatomic points 164, 166 and 168.

Figure 7:
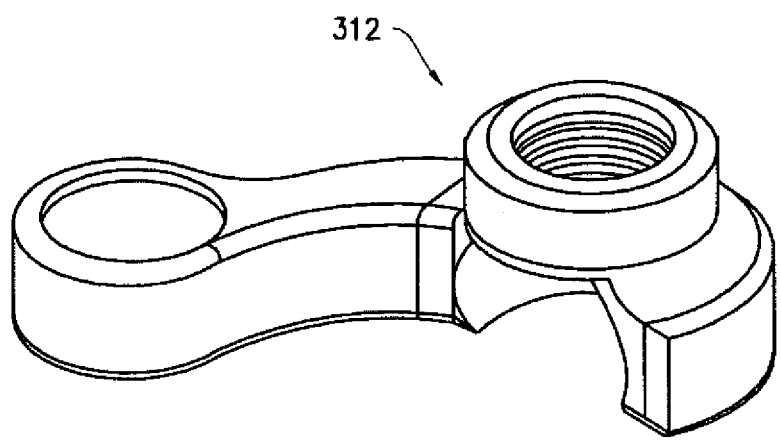
FIG. 7 illustrates a linkage frame included in the assembly of FIG. 6.
Figure 8:
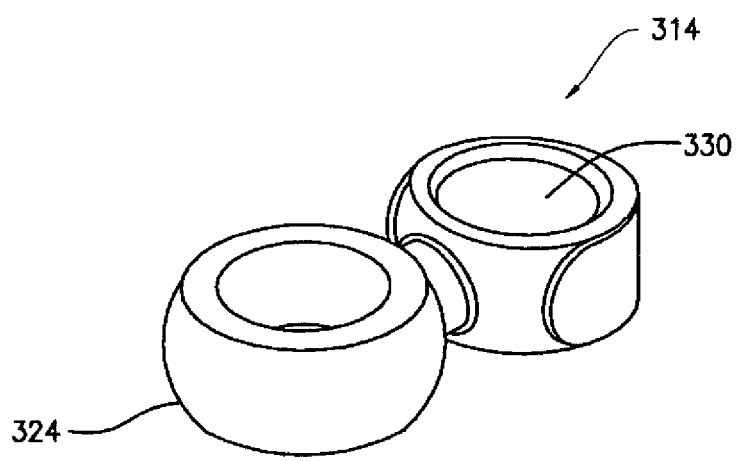
FIG. 8 illustrates an articulating linkage included in the assembly of FIG. 6.

FIGS. 6, 6A, 6B and 6C show various views of an assembly of a rod contouring alignment linkage 310 (the alignment linkage 310). The alignment linkage 310 is used to ensure that the extenders 180A, 182A and 188A (or 180, 182 and 188) are parallel to each other. Hereafter only 180A, 182A and 188A are mentioned, however, the discussion hereafter applies equally to extenders 180, 182 and 188. The alignment linkage 310 includes a linkage frame 312 (see FIG. 7), an articulating linkage 314 (see FIG. 8) and a locking member 316. The linkage frame 312 includes an arm 318 having a bore 320. The bore 320 is adapted to receive one of the extenders 180A, 182A and 188A. The linkage frame 312 also includes a spherical cutout 322 that receives the articulating linkage 314. The spherical cutout 322 allows the articulating linkage 314 to have all rotational degrees of freedom and thereby allows it to adapt to any varying trajectories of extenders 180A, 182A and 188A.

The articulating linkage 314 includes a partial spherical ball 324 that mates with the spherical cutout 322. The ball 324 has a conical tapered cutout 326 and a cylindrical bore 328 concentric with the conical tapered cutout 326. The articulating linkage 314 has a second bore 330 at the opposing end from the cylindrical bore 328. The second bore 330 is adapted to receive one of the extenders 180A, 182A and 188A. The bores 320 and 330 in the alignment linkage 310 constrain only the appropriate degrees of freedom of the extenders to align two of the extenders 180A, 182A and 188A in a parallel orientation. At the same time, the alignment linkage 310 does not constrain other degrees of freedom such as rotation about or translation along the central axis of the extenders 180A, 182A and 188A.

Figure 9:
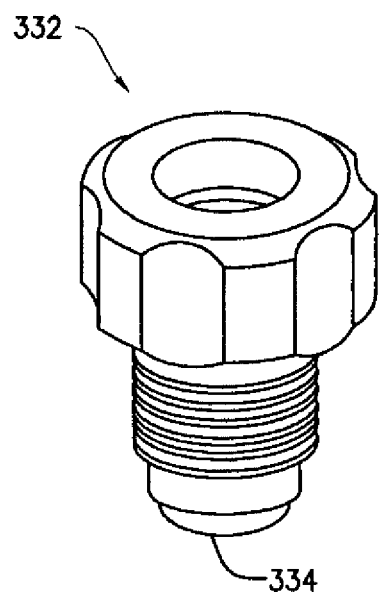
FIG. 9 illustrates a thumb screw with a conical tip included in the assembly of FIG. 6.
Figure 10:
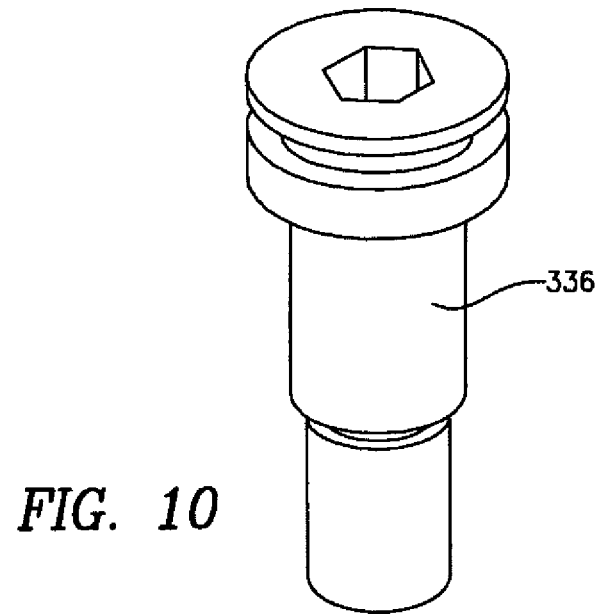
FIG. 10 illustrates a spring loaded pin included in the assembly of FIG. 6.
Figure 11:
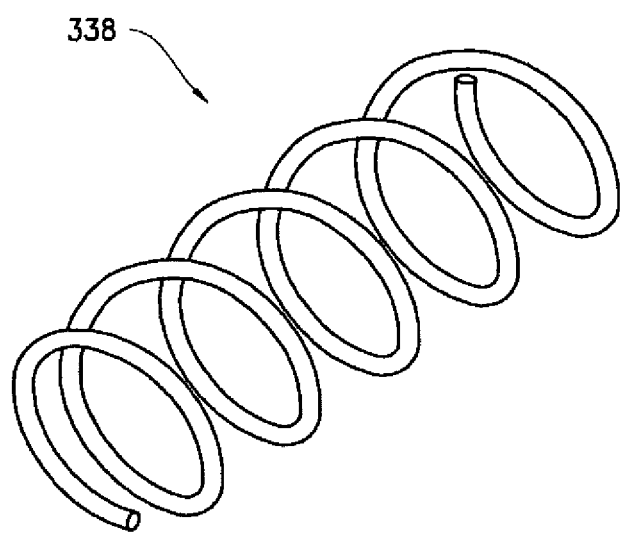
FIG. 11 illustrates a spring included in the assembly of FIG. 6.
Figure 12:
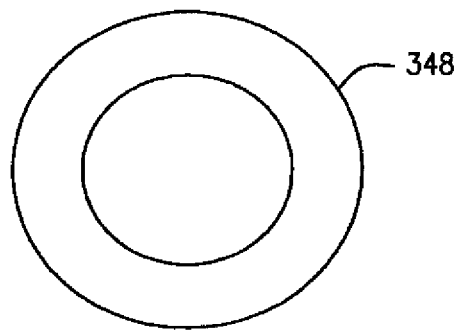
FIG. 12 illustrates an o-ring included in the assembly of FIG. 6.
Figure 13:
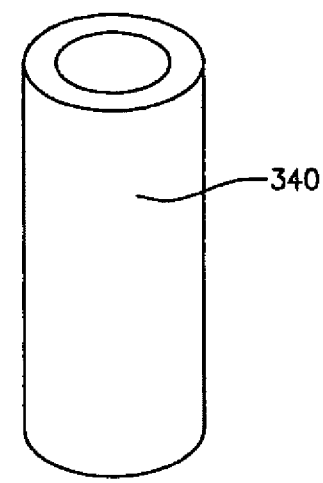
FIG. 13 illustrates a hollow cylinder 340 included in the assembly of FIG. 6.

The locking member 316 (FIG. 6) includes a thumb screw 332 (see FIG. 9) with a conical tip 334 and a spring loaded pin 336 (FIG. 10) engaged in a bore 346 in the centre of the thumb screw 332. The spring loaded pin assembly includes the spring loaded pin 336, spring 338 (see FIG. 11), an o-ring 348 (see FIG. 12) and a hollow cylinder 340 (see FIG. 13). The tip of the spring loaded pin 336 is insertable in the central bore 342 in the hollow cylinder 340. When the spring loaded pin 336 and the hollow cylinder 340 are assembled in the locking member 316, spring 338 is captured in the bore 346 between the pin 336 and the hollow cylinder 340. The conical tip 334 engages with the conical tapered cutout 326. Since the articulating linkage 314 can rotate, the alignment linkage 310 can be used with varying intrapedicular distances. The spring loaded pin 336 snaps into the cylindrical bore 328 of the articulating linkage 314 when the articulating linkage 314 and linkage frame 318 are locked via tightening of thumb screw 332.

Figure 14A:
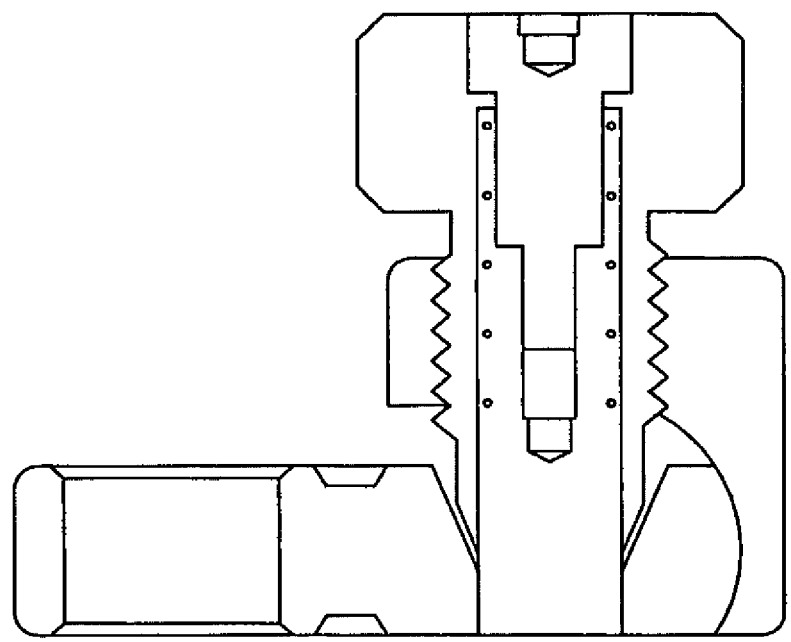
FIGS. 14A, 14B, 14C and 14D illustrate the details of the pop-up indicator under various states of alignment of the extenders.
Figure 14B:
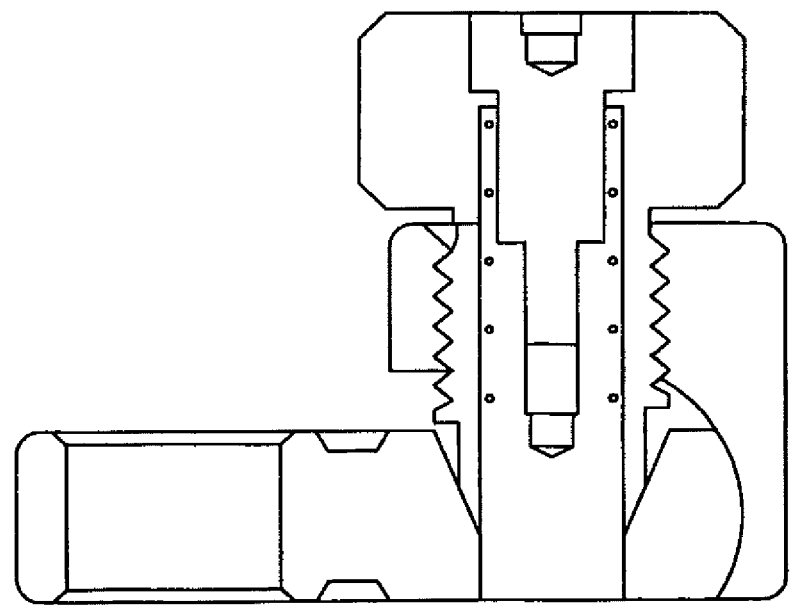

FIGS. 14A, B, C, D show the details of the pop-up indicator provided by the spring loaded pin 336. The pop-up indicator notifies the users when the locking member 316 is tightened with two of the extenders 180A, 182A and 188A in non-parallel configuration. FIGS. 14A, B C, D shows the locking member 316 in various stages of use. FIG. 14A shows the locking member 316 being tightened with the extenders attached to the alignment linkage 310 in a parallel position. In this instance the conical tip 334 aligns with the conical cutout 326 (see FIG. 14B) and the extenders are locked in the parallel position.

Figure 14C:
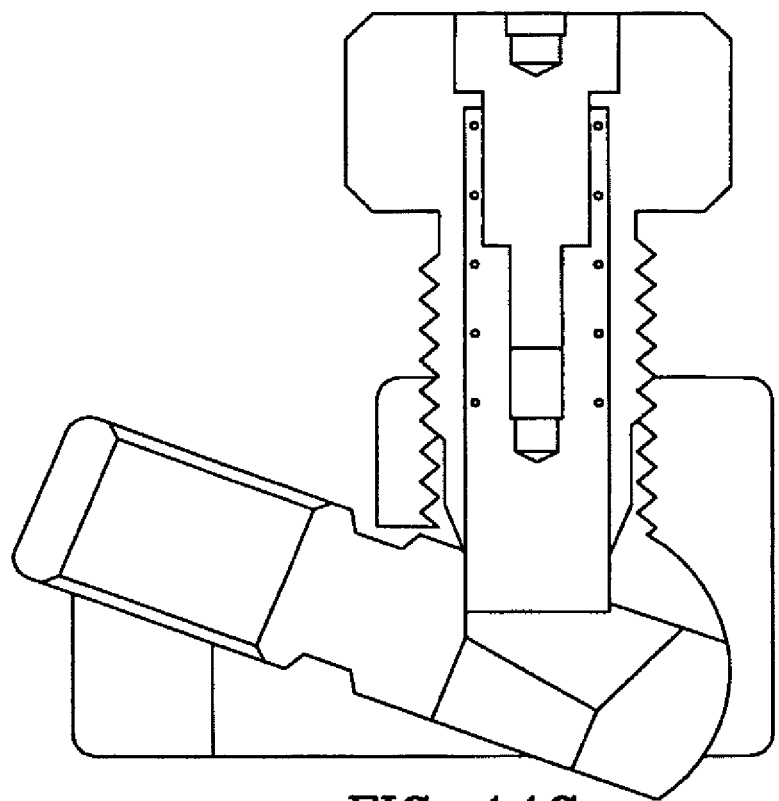
Figure 14D:
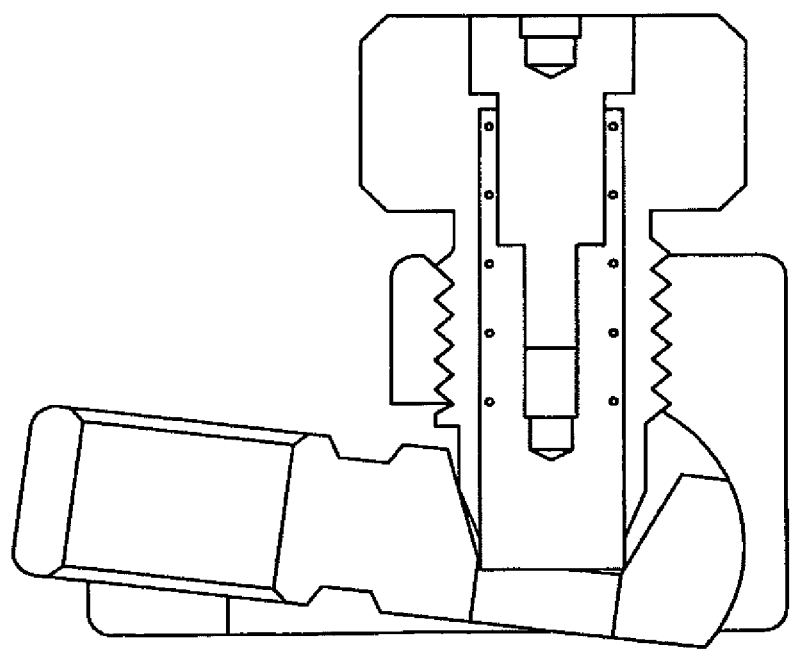
Figure 15:
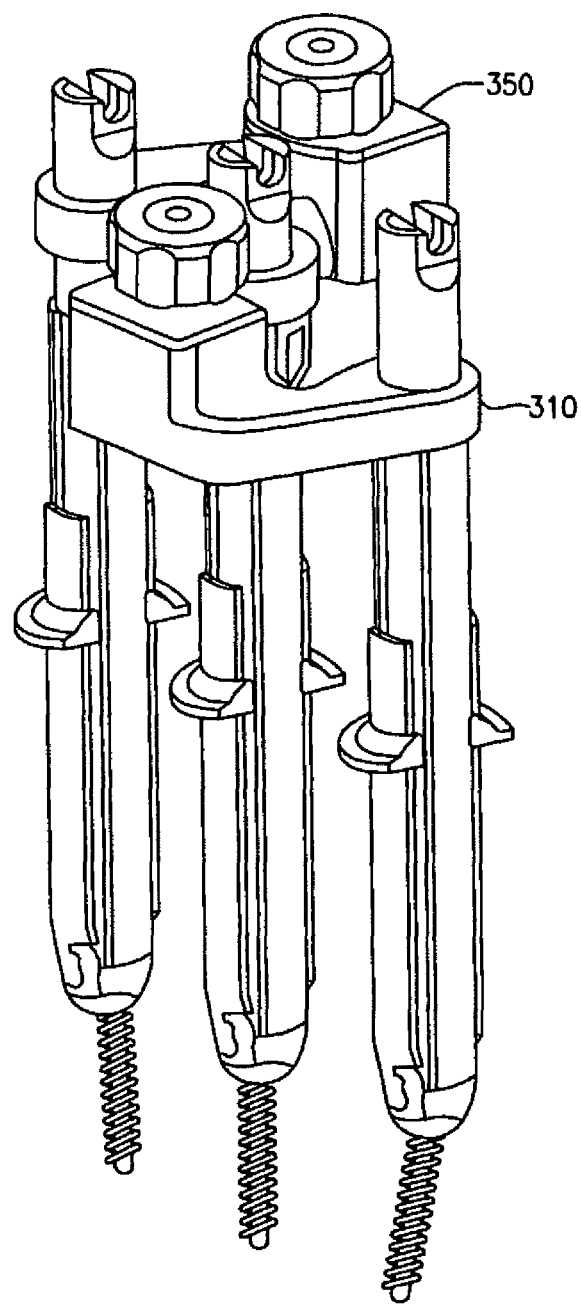
FIG. 15 is a perspective view showing three extenders being aligned using two alignment linkages.

FIG. 14C illustrates a case when the locking member 316 is being tightened and the extenders attached to the alignment linkage 310 are grossly un-parallel. In this instance the locking member 316 may not advance easily. However, as seen in FIG. 14D, if the extenders attached to the alignment linkage 310 are slightly un-parallel, the locking member 316 would advance. When the locking member 316 is advanced, the hollow cylinder 340 is also advanced. However, the un-parallel position of extenders results in the cylinder 340 not being aligned with bore 328, which in turn leads to the cylinder 340 hitting the conical tapered cutout 326. Once the cylinder 340 touches the conical tapered cutout 326 and locking member 316 is advanced further thereafter, spring 338 is compressed leading to pop-out of the pin 336. The pop-out of the pin 336 indicates to the surgeon that the extenders are not in parallel orientation and that the surgeon should bring the extenders in parallel orientation and thereafter tighten the locking member 316 to lock the extenders in parallel orientation. Once the first and second extenders are locked in parallel position, the process is repeated using a second alignment linkage 350 (see FIG. 15) to lock the second and the third extender in mutually parallel position. The extenders 180A, 182A and 188a could be manipulated by the surgeon to make them parallel to each other and thereafter alignment linkages could be tightened to lock the extenders 180A, 182A and 199A in parallel position.

Once the alignment linkages 310, 350 have been applied, the extenders 180A, 182A and 188A are locked parallel. The projected points 214, 216 and 218 then mimic the relative positioning of the anatomic points 164, 166 and 168, respectively, within the body. Thus, the extenders 180A, 182A and 188A apply a translational spatial transformation to the anatomic points 164, 166 and 168 to move them to a more accessible location without altering their positions relative to each other. Accordingly, a rod contoured such that its axis passes through the projected points 214, 216 and 218 may be installed such that its axis passes through the anatomic points 164, 166 and 168 to properly extend through the cages 152 of the pedicle screws 140, 142 and 148.

Figure 16:
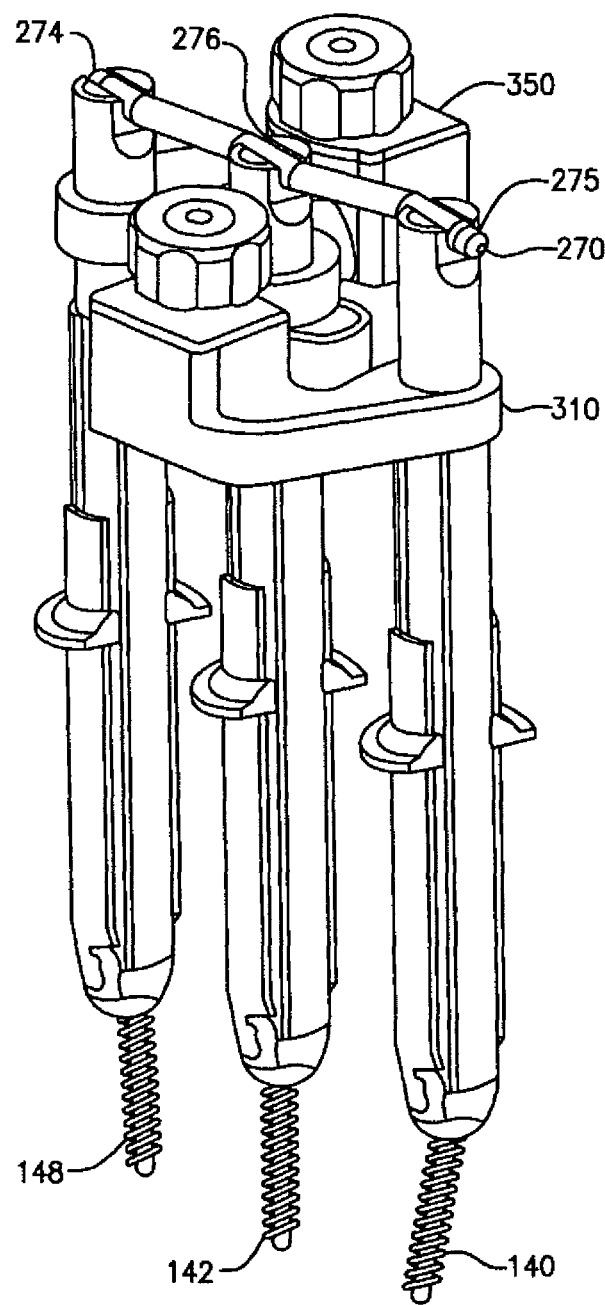
FIG. 16 is a perspective view of the pedicle screws, the extenders, and the alignment linkages, with a rod seated in the rod interfaces of the extenders.

Referring to FIG. 16, a perspective view illustrates the pedicle screws 140, 142 and 148, the extenders 180A, 182A and 188A, and the alignment linkages 310 and 350, with a rod 270 seated in the rod interfaces 200 of the extenders 180A, 182A and 188A for contouring. The rod 270 has a first end 272, a second end 274, and a central portion 276. As shown, the first end 272 is positioned in the rod interface 200 of the first extender 180A, the central portion 276 is positioned in the rod interface 200 of the second extender 182A, and the second end 274 is positioned in the rod interface 200 of the third extender 188A.

Due to natural variations in spinal morphology, the cages 152 of the pedicle screws 140, 142 and 148 may not be arranged in a straight line. Thus, the rod interfaces 200 may not be arranged in a straight line. Thus, rod 270 may need to be bent into the proper shape, for example, through the use of tooling such as pliers, a vice, or the like, so that it will lie properly within the rod interfaces 200. The process of deforming the rod 270 to the required shape may be termed "contouring."

Contouring may be carried out by, first, placing the undeformed rod 270 in the rod interfaces 200 to determine how the rod 270 should be deformed to lay properly within the rod interfaces 200. Then, the rod 270 is deformed, and again placed in the rod interfaces 200 to check the fit. This process is repeated until the rod 270 is shaped to provide and optimal fit with the rod interfaces 200.

In the alternative to contouring, the rod 270 may simply be selected from a kit or like. For example, such a kit may include rods bent at a variety of angles. The rod interfaces 200 could be used to select the proper rod from the kit by placing each rod, in turn, on the rod interfaces 200 until one is identified that has the proper fit. As another alternative, the rod 270 may be custom fabricated, for example, by measuring the relative positions of the rod interfaces 200 and using a CNC procedure to form the rod 270.

After the rod 270 has been configured or selected, the rod 270 and the extenders 180A, 182A and 188A may be removed from the operating site, leaving the pedicle screws 140, 142 and 148 in place. The cannulas 100, 102 and 108 or intermediate pieces 80, if used, may also be removed at this stage, depending on the method that will be used to implant the rod 270. The rod 270 may be inserted subcutaneously and placed on the cages 152 by making additional incisions to connect the access passageways provided by the cannulas 100, 102 and 108. Alternatively, MIS (Minimally Invasive Surgical) techniques may be used to implant the rod 270 without making additional major incisions.

Figure 17:
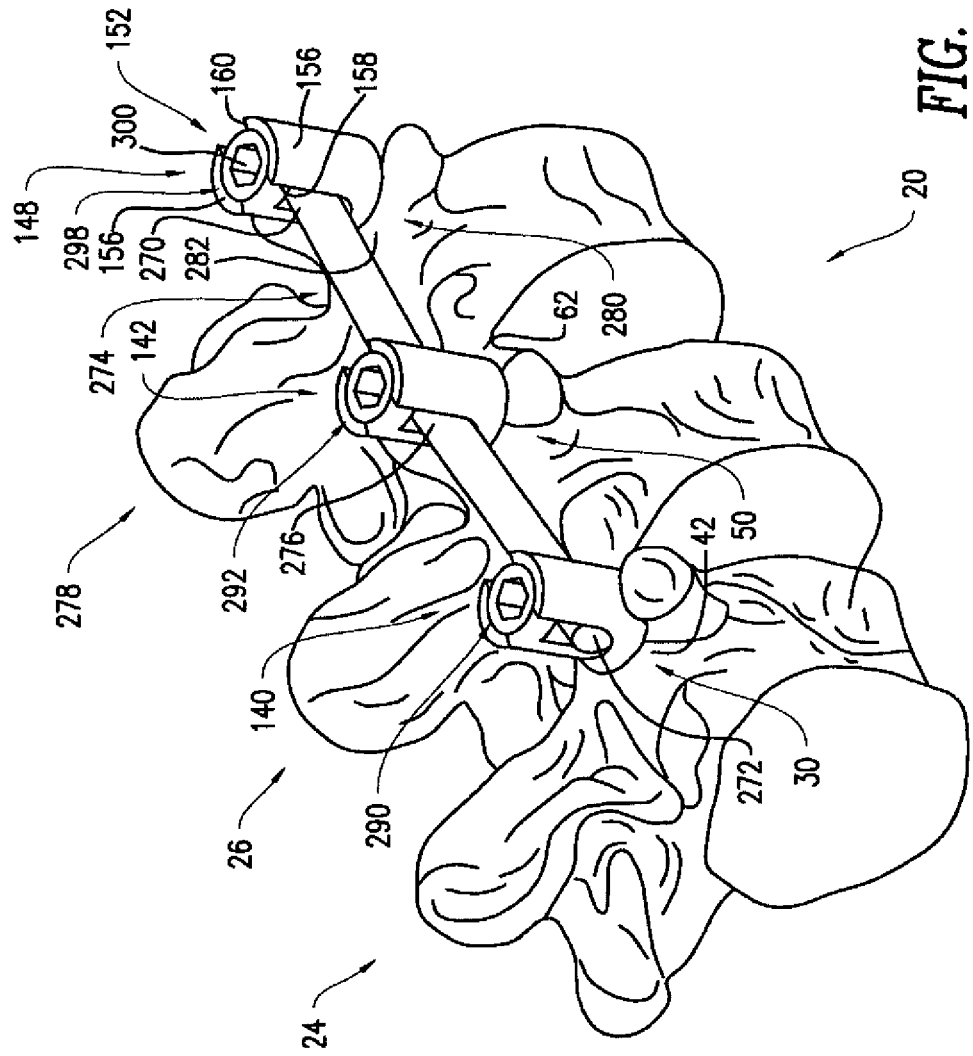
FIG. 17 is a perspective view of three adjacent vertebrae of the spine, with the rod secured to the pedicle screw to provide posterior spinal fusion.

Referring to FIG. 17, a perspective view illustrates the completed posterior spinal fusion system. In addiction to the first and second vertebrae 24, 26, FIG. 17 illustrates a third vertebra 278 superior to the second vertebra 26. The third vertebra 278 has features similar to those set fourth in the description of the first and second vertebrae 24, 26. Most pertinently, the third vertebra 278 has pedicles 280 with saddle points 282.

As shown, the first pedicle screw 140 is implanted in the pedicle 30 of the right side of the first vertebra 24, the second pedicle screw 142 is implanted in the pedicle 50 of the right side of the second vertebra 26, and the third pedicle screw 148 is implanted in the pedicle 280 of the right side of the third vertebra 278. The rod 270 passes through the slots 158, 160 of the cages 152, in such a manner that the axis (not shown) of the rod 270 passes through the anatomic points 164, 166 and 168.

First, second, and third nuts 290, 292 and 298 have been rotated into engagement with the inward-facing surfaces of the arms 156 of the cages 152 of the first, second, and third pedicle screws 140, 142 and 148, respectively. The nuts 290, 292 and 298 have been tightened to press the first end 272, central portion 276, and second end 274, respectively, against the heads of the screws 154 of the pedicle screws 140, 142 and 148, respectively. Thus, the cages 152 are no longer freely rotatable with respect to the screws 154, but are instead locked in their current orientations.

The pedicle screws 140, 142 and 148 thus cooperate with the rod 270 to restrict relative motion of the vertebrae 24, 26 and 278 to form a posterior vertebral fusion system. If desired, a similar system may be implanted in the left-side pedicles 30, 50 and 280 of the vertebrae 24, 26 and 278 through the method set forth previously to provide a bilateral system. Additionally, the present invention is not limited to a three-level fusion system, but may be used to fuse any number of vertebrae together. To fuse more than three vertebrae together, the steps set forth above may simply be repeated for each additional vertebra, and the rod may be placed on four or more rod interfaces for configuration or selection.

The alignment linkage system may also be used with minimally invasive surgery described in commonly assigned patent application filed on even date and entitled "ROD CONTOURING APPARATUS AND METHOD FOR PERCUTANEOUS PEDICLE SCREW EXTENSION," filed Sep. 25, 2006, Ser. No. 11/526,785, which is hereby incorporated by reference in its entirety.

The foregoing is only one of many methods encompassed within the scope of the present invention. According to one alternative method, the cannulas 100, 102 and 108 or intermediate pieces 80 may be omitted entirely from the procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for projecting anatomic points located within a patient's body outside the patient's body, the system comprising:
a first extender having a distal end configured to connect to a first pedicle screw such that the first extender extends proximally therefrom along a first longitudinal axis;
a second extender having a distal end configured to connect to a second pedicle screw such that the second extender extends proximally therefrom along a second longitudinal axis, the first and second longitudinal axes extending along an anterior-posterior direction; and
an alignment linkage for coupling together the first extender and the second extender, the alignment linkage comprising:
a first arm having a first connector, the first connector having a first opening configured to receive the first extender therein; and
a second arm having a second connector, the second connector having a second opening configured to receive the second extender therein;
wherein the first arm and the second arm are coupled together in the alignment linkage such that the first and second arms are pivotable relative to one another about a plurality of pivot axes passing through a pivot point, a first one of the plurality of pivot axes extending along the anterior-posterior direction, and the first pivot axis not being along the first extender, the second extender, or another extender when the first and second openings receive the respective first and second extenders therein.

2. The system of claim 1, wherein the first opening of the first connector is configured to receive the first extender such that the first arm is rotatable about the first longitudinal axis of the first extender, and wherein the second opening of the second connector is configured to receive the second extender such that the second arm is rotatable about the second longitudinal axis of the second extender.

3. The system of claim 1, wherein the first opening of the first connector is configured to receive the first extender such that the first arm extends orthogonally to the first longitudinal axis of the first extender, and wherein the second opening of the second connector is configured to receive the second extender such that the second arm extends orthogonally to the second longitudinal axis of the second extender.

4. The system of claim 1, wherein the first and second arms are connected to each other at the pivot point.

5. The system of claim 4, wherein the first arm has a proximal end and a distal end, the first connector being located at the distal end of the first arm and the pivot point being located at the proximal end of the first arm, and wherein the second arm has a proximal end and a distal end, the second connector being located at the distal end of the second arm and the pivot point being located at the proximal end of the second arm.

6. The system of claim 1, further comprising a lock configured to lock the first and second arms with respect to one another such that the relative orientation between the first and second extenders is fixed when the first and second extenders are received in the respective first and second openings of the first and second arms.

7. The system of claim 6, wherein the lock comprises a locking screw configured to move between a locked configuration and an unlocked configuration by rotational advancement.

8. The system of claim 1, wherein, when the alignment linkage is coupled to the first and second extenders, the pivot point is spaced laterally of a plane defined by the first and second extenders.

9. A system for projecting anatomic points located within a patient's body outside the patient's body, the system comprising:
a first extender having a distal end configured to connect to a first pedicle screw such that the first extender extends proximally therefrom along a first longitudinal axis;
a second extender having a distal end configured to connect to a second pedicle screw such that the second extender extends proximally therefrom along a second longitudinal axis, the first and second longitudinal axes extending along an anterior-posterior direction; and
an alignment linkage for coupling together the first extender and the second extender, the alignment linkage comprising:
a first arm having a first connector, the first connector being connectable to the first extender such that the first arm is rotatable about the first longitudinal axis of the first extender; and
a second arm having a second connector, the second connector being connectable to the second extender such that the second arm is rotatable about the second longitudinal axis of the second extender;
wherein the first arm and the second arm are coupled together in the alignment linkage such that the first and second arms are pivotable relative to one another about a plurality of pivot axes passing through a pivot point, a first one of the plurality of pivot axes extending along the anterior-posterior direction, and the first pivot axis not being along the first extender, the second extender, or another extender when the first and second connectors are connected to the respective first and second extenders.

10. The system of claim 9, wherein the first connector is connectable to the first extender such that the first arm extends orthogonally to the first longitudinal axis of the first extender, and wherein the second connector is connectable to the second extender such that the second arm extends orthogonally to the second longitudinal axis of the second extender.

11. The system of claim 9, wherein the first and second arms are connected to each other at the pivot point.

12. The system of claim 11, wherein the first arm has a proximal end and a distal end, the first connector being located at the distal end of the first arm and the pivot point being located at the proximal end of the first arm, and wherein the second arm has a proximal end and a distal end, the second connector being located at the distal end of the second arm and the pivot point being located at the proximal end of the second arm.

13. The system of claim 9, further comprising a lock configured to lock the first and second arms with respect to one another such that the relative orientation between the first and second extenders is fixed when the first and second extenders are connected to the respective first and second connectors of the first and second arms.

14. The system of claim 13, wherein the lock comprises a locking screw configured to move between a locked configuration and an unlocked configuration by rotational advancement.

15. The system of claim 9, wherein, when the alignment linkage is coupled to the first and second extenders, the pivot point is spaced laterally of a plane defined by the first and second extenders.

16. A system for projecting anatomic points located within a patient's body outside the patient's body, the system comprising:
a first extender having a distal end configured to connect to a first pedicle screw such that the first extender extends proximally therefrom along a first longitudinal axis;
a second extender having a distal end configured to connect to a second pedicle screw such that the second extender extends proximally therefrom along a second longitudinal axis, the first and second longitudinal axes extending along an anterior-posterior direction; and
an alignment linkage for coupling together the first extender and the second extender, the alignment linkage comprising:
a first arm having a first connector, the first connector being connectable to the first extender such that the first arm extends orthogonally to the first longitudinal axis of the first extender; and
a second arm having a second connector, the second connector being connectable to the second extender such that the second arm extends orthogonally to the second longitudinal axis of the second extender;
wherein the first arm and the second arm are coupled together in the alignment linkage such that the first and second arms are pivotable relative to one another about a plurality of pivot axes passing through a pivot point, a first one of the plurality of pivot axes extending along the anterior-posterior direction, and the first pivot axis not being along the first extender, the second extender, or another extender when the first and second connectors are connected to the respective first and second extenders.

17. The system of claim 16, wherein the first and second arms are connected to each other at the pivot point.

18. The system of claim 17, wherein the first arm has a proximal end and a distal end, the first connector being located at the distal end of the first arm and the pivot point being located at the proximal end of the first arm, and wherein the second arm has a proximal end and a distal end, the second connector being located at the distal end of the second arm and the pivot point being located at the proximal end of the second arm.

19. The system of claim 16, further comprising a lock configured to lock the first and second arms with respect to one another such that the relative orientation between the first and second extenders is fixed when the first and second extenders are connected to the respective first and second connectors of the first and second arms.

20. The system of claim 19, wherein the lock comprises a locking screw configured to move between a locked configuration and an unlocked configuration by rotational advancement.

21. The system of claim 16, wherein, when the alignment linkage is coupled to the first and second extenders, the pivot point is spaced laterally of a plane defined by the first and second extenders.

* * * * *

UNITED STATES PATENT AND TRADEMARK OFFICE
CERTIFICATE OF CORRECTION

PATENT NO. : 10,085,807 B2  
APPLICATION NO. : 14/662988  
DATED : October 2, 2018  
INVENTOR(S) : Joshua A. Butters and Jeffery Arnett Page 1 of 1

It is certified that error appears in the above-identified patent and that said Letters Patent is hereby corrected as shown below:

On the Title Page

In Item (22), the filing date "Aug. 3, 2015" should read --Mar. 19, 2015--.

Signed and Sealed this  
Twenty-seventh Day of November, 2018

Andrei Iancu  
*Director of the United States Patent and Trademark Office*